United States Patent
Niwayama et al.

(10) Patent No.: US 10,081,735 B1
(45) Date of Patent: Sep. 25, 2018

(54) CONDUCTIVE LIQUID COMPOSITION

(71) Applicant: Teikoku Printing Inks Mfg. Co., Ltd., Tokyo (JP)

(72) Inventors: Yuka Niwayama, Tokyo (JP); Miki Hosoda, Tokyo (JP); Hiroyoshi Shinjyo, Tokyo (JP)

(73) Assignee: Teikoku Printing Inks Mfg. Co. Ltd., Tokyo (JP)

( * ) Notice: Subject to any disclaimer, the term of this patent is extended or adjusted under 35 U.S.C. 154(b) by 0 days.

(21) Appl. No.: 15/328,764

(22) PCT Filed: Sep. 2, 2016

(86) PCT No.: PCT/JP2016/075877
§ 371 (c)(1),
(2) Date: Jan. 24, 2017

(87) PCT Pub. No.: WO2018/042635
PCT Pub. Date: Mar. 8, 2018

(51) Int. Cl.
| | |
|---|---|
| *H01B 1/24* | (2006.01) |
| *C09D 11/52* | (2014.01) |
| *C09D 5/24* | (2006.01) |
| *C09D 11/102* | (2014.01) |
| *C08L 71/08* | (2006.01) |
| *C08K 3/36* | (2006.01) |
| *C08K 3/04* | (2006.01) |
| *C07F 7/22* | (2006.01) |
| *C08K 5/57* | (2006.01) |
| *B41F 17/00* | (2006.01) |
| *C08L 75/02* | (2006.01) |
| *C08L 75/04* | (2006.01) |

(52) U.S. Cl.
CPC .......... *C09D 11/102* (2013.01); *C07F 7/2232* (2013.01); *C08K 3/04* (2013.01); *C08K 3/36* (2013.01); *C08K 5/57* (2013.01); *C08L 71/08* (2013.01); *B41F 17/001* (2013.01); *C08F 2500/02* (2013.01); *C08L 75/02* (2013.01); *C08L 75/04* (2013.01)

(58) Field of Classification Search
CPC ............. C09D 5/24; C09D 11/52; H01B 1/24
See application file for complete search history.

(56) References Cited

FOREIGN PATENT DOCUMENTS

| | | | |
|---|---|---|---|
| JP | 54-36343 | A | 3/1979 |
| JP | 1-159905 | A | 6/1989 |
| JP | 2005-259546 | A | 9/2005 |
| JP | 2005259546 | A * | 9/2005 |
| JP | 2010-539650 | A | 12/2010 |
| JP | 2011-526309 | A | 10/2011 |
| JP | 2012-246433 | A | 12/2012 |
| JP | 2014-181316 | A | 9/2014 |
| JP | 2014181316 | A * | 9/2014 |
| JP | 2015-230847 | A | 12/2015 |
| JP | 2015230847 | A * | 12/2015 |
| JP | 2016-513143 | A | 5/2016 |
| WO | 2011/046076 | A1 | 4/2011 |

OTHER PUBLICATIONS

Machine-generated English translation of JP-2014181316-A (Sep. 2014).*
Machine-generated English translation of JP-2005259546-A (Sep. 2005).*
Machine-generated English translation of JP-2015230847-A (Dec. 2015).*

* cited by examiner

*Primary Examiner* — Vu A Nguyen
(74) *Attorney, Agent, or Firm* — Richard M. Goldberg

(57) ABSTRACT

A conductive liquid composition includes:
for a binder resin, 5 to 25 mass % of hydroxyl-containing resin with hydroxyl value 3 to 100 and weight-average molecular weight 4000 to 20000,
for a solvent, at least one solvent with a boiling point ≥170° C., ≥70 mass % of the total solvent,
for a curing agent, 1.5 to 10.0 mass % of polyisocyanate,
(D) for a curing accelerator, 0.005 to 0.1 mass % of organometallic compound,
(E) for an adhesion reinforcing agent, 0.2 to 2.5 mass % of coupling agent,
(F) for conducting materials:
(f1) 2.0 to 10.0 mass % of graphite,
(f2) 5.0 to 15.0 mass % of conductive carbon black, and
(f3) 20.0 to 50.0 mass % of silica particles with a mean particle size 1.0 to 7.0 μm and surface-coated with silver, and
(G) a surface resistivity 1 to 1000 Ω/sq. when the thickness of the cured film of the conductive liquid composition is 8 μm.

9 Claims, No Drawings

CONDUCTIVE LIQUID COMPOSITION

TECHNICAL FIELD

The present invention relates in particular to a conductive liquid composition that can be applied for both flexible plastic film substrates and glass substrates, the conductive liquid composition being usable for antistatic purposes and for electromagnetic wave shields. The invention further relates to a conductive liquid composition having an antistatic function and an electromagnetic wave shield function that exhibits a very excellent leveling property (surface smoothness) as a coated film even with a thin film thickness of about 8 to 10 μm, and also excellent resistance to rinsing with organic solvents such as MEK.

BACKGROUND ART

Conductive liquid compositions are used in the production of semiconductor packages and microelectronic devices and in assembly, for various purposes including antistatic functions, electromagnetic wave shield functions and anisotropic conductive adhesive functions (die mounting adhesives and the like).

With the introduction of flexible display terminals in recent years, and as conventional electronic terminals continue to decrease in thickness, the substrates that are coated with conductive liquid compositions are becoming ever more diverse and include different types of flexible plastic substrates and thin glass substrates.

Furthermore, as thicknesses decrease as is above described, the coating layers of the conductive liquid compositions are also becoming thinner, and for solid patterns with low thicknesses of about 5 to 10 μm and wide areas (for example, about 50 mm×80 mm), it is becoming increasingly difficult to achieve uniform and highly smooth surfaces for the conductive liquid composition coating layers, which has resulted in the problem of variation in conductive functioning at the coating layer locations.

Incidentally, the surface smoothness of a coated film tends to be improved when the conductive liquid composition coating layer is a thick film of about not less than an extent from 15 to 25 μm, but this solution not only increases the amount of conductive liquid composition used and results in higher cost, but also interferes with the aforementioned decrease in thickness.

In light of this situation, the performance required for conductive liquid compositions naturally includes the ability for a single type of conductive liquid composition to be used in common for plastic substrates including flexible sheets and the like and conventional glass, and a conductive function that ensures adequate performance for the purpose even with a low film thickness, as well as a high leveling property (surface smoothness) to exhibit a uniform conductive function without fine irregularities even with thin coated films, and the ability to adequately withstand rinsing with MEK and the like that are used for removal of trace contamination. However, it is clear from the prior art literature cited below that, as of the current time, no conductive liquid composition has yet been developed that simultaneously exhibits the aforementioned required performance to a satisfactory extent.

Prior Patent Document 1 (Japanese Unexamined Patent Application Publication No. 2015-230847) discloses metal covered particles with high conductivity and a conductive resin composition containing the metal covered particles, but it does not disclose technology relating to a conductive liquid composition that can be used in common for plastic substrates and glass substrates, nor does it disclose technology relating to formation of a coated film with a high degree of surface smoothness even as a thin-film, and able to adequately withstand organic solvent rinsing.

Prior Patent Document 2 (Japanese Patent Public Inspection No. 2016-513143) discloses technology relating to a conductive ink composition that is satisfactory for flexible film substrates, but it does not disclose technology allowing common use for glass substrates as well, or technology relating to formation of a coated film with a high degree of surface smoothness even as a thin-film, and able to withstand organic solvent rinsing.

Prior Patent Document 3 (Japanese Patent Public Inspection No. 2010-539650) discloses a conductive composition including a binder and filler particles with a silver plated core, the composition having a sheet resistivity of not more than about 0.100 Ω/sq./25 μm, but it does not disclose technology allowing common use for both plastic substrates and glass substrates, or technology relating to formation of a coated film with a high degree of surface smoothness even as a thin-film, and able to withstand organic solvent rinsing.

Prior Patent Document 4 (Japanese Patent Public Inspection No. 2011-526309) discloses a conductive curable composition filled with a silver-coated flaky material, the disclosure also relating to the viscosity and thixotropic property of the composition. However, it does not disclose technology allowing common use for both plastic substrates and glass substrates, nor does it disclose technology relating to formation of a coated film with a high degree of surface smoothness even as a thin-film, and able to withstand organic solvent rinsing.

CITATION LIST

Patent Document

Prior Patent Document 1: Japanese Unexamined Patent Application Publication No. 2015-230847
Prior Patent Document 2: Japanese Patent Public Inspection No. 2016-513143
Prior Patent Document 3: Japanese Patent Public Inspection No. 2010-539650
Prior Patent Document 4: Japanese Patent Public Inspection No. 2011-526309

SUMMARY OF THE INVENTION

Problem to be Solved by the Invention

The present invention has been devised in light of the problems mentioned above, and as a technology that has no previous disclosure, it relates to a conductive liquid composition that can be used as a single type of conductive liquid composition for plastic substrates such as flexible sheets and films, and conventional glass, that has a conductive function exhibiting adequate performance for a given purpose even with a low film thickness, and also a high leveling property (surface smoothness) to exhibit a uniform conductive function without fine irregularities even with thin coated films, and that can form a coating layer with the ability to withstand rinsing with MEK and the like used for removal of trace contamination, as well as an article having a coating layer of the conductive liquid composition and a method for producing the article.

Means for Solving the Problems

The present invention relates to a conductive liquid composition comprising:

(A) containing, for a binder resin, from 5 to 25 mass % of a hydroxyl-containing resin with a hydroxyl value from 3 to 100 and a weight-average molecular weight from 4000 to 20000, (B) containing, for a solvent, one or two more types of solvents with boiling points of not less than 170° C. selected from among isophorone, dibasic acid esters, 3-methoxy-3-methylbutanol, 3-methoxy-3-methylbutyl acetate, ethyleneglycol monobutyl ether acetate, coal tar naphtha with a boiling point of more than 170° C., diethyleneglycol monoethyl ether, diethyleneglycol monoethyl ether acetate, diethyleneglycol monobutyl ether, diethyleneglycol monobutyl ether acetate, triethyleneglycol monobutyl ether, triethyleneglycol monobutyl ether acetate, polyethyleneglycol dimethyl ether, tetraethyleneglycol dimethyl ether and polyethyleneglycol monomethyl ether, at not less than 70 mass % of the total solvent, (C) containing, for a curing agent, from 1.5 to 10.0 mass % of polyisocyanate, (D) containing, for a curing accelerator, from 0.005 to 0.1 mass % of an organometallic compound, (E) containing, for an adhesion reinforcing agent, from 0.2 to 2.5 mass % of a coupling agent, (F) containing, for conducting materials:
(f1) from 2.0 to 10.0 mass % of graphite,
(f2) from 5.0 to 15.0 mass % of conductive carbon black, and
(f3) from 20.0 to 50.0 mass % of silica particles with a mean particle size from 1.0 to 7.0 μm and surface-coated with silver, and (G) having a surface resistivity from 1 to 1000 Ω/sq. when the thickness of the cured film of the conductive liquid composition is 8 μm.

Effects of the Invention

With the conductive liquid composition of the invention, it has become possible to obtain a conductive liquid composition that can be used as a single type of conductive liquid composition for plastic substrates including flexible sheets and the like, and conventional glass substrates, that has an adequate electromagnetic wave shield function and antistatic function even with a low film thickness, and also a high leveling property (surface smoothness) even as a thin coated film, and can form a coating layer with the ability to adequately withstand rinsing with MEK and the like used for removal of trace contamination, as well as an article having a coating layer of the conductive liquid composition and a method for producing the article.

MODE FOR CARRYING OUT THE INVENTION

As mentioned above, the invention relates to a conductive liquid composition comprising:

(A) containing, for a binder resin, from 5 to 25 mass % of a hydroxyl-containing resin with a hydroxyl value from 3 to 100 and a weight-average molecular weight from 4000 to 20000, (B) containing, for a solvent, one or two more types of solvents with boiling points of not less than 170° C. selected from among isophorone, dibasic acid esters, 3-methoxy-3-methylbutanol, 3-methoxy-3-methylbutyl acetate, ethyleneglycol monobutyl ether acetate, coal tar naphtha with a boiling point of more than 170° C., diethyleneglycol monoethyl ether, diethyleneglycol monoethyl ether acetate, diethyleneglycol monobutyl ether, diethyleneglycol monobutyl ether acetate, triethyleneglycol monobutyl ether, triethyleneglycol monobutyl ether acetate, polyethyleneglycol dimethyl ether, tetraethyleneglycol dimethyl ether and polyethyleneglycol monomethyl ether, at not less than 70 mass % of the total solvent, (C) containing, for a curing agent, from 1.5 to 10.0 mass % of polyisocyanate, (D) containing, for a curing accelerator, from 0.005 to 0.1 mass % of an organometallic compound, (E) containing, for an adhesion reinforcing agent, from 0.2 to 2.5 mass % of a coupling agent, (F) containing, for conducting materials:
(f1) from 2.0 to 10.0 mass % of graphite,
(f2) from 5.0 to 15.0 mass % of conductive carbon black, and
(f3) from 20.0 to 50.0 mass % of silica particles with a mean particle size from 1.0 to 7.0 μm and surface-coated with silver, and (G) having a surface resistivity from 1 to 1000 Ω/sq. when the thickness of the cured film of the conductive liquid composition is 8 μm.

The invention further relates to a conductive liquid composition wherein the viscosity of the conductive liquid composition is from 0.1 to 100 Pa·s when measured at 25±1° C. by a BH-type rotating viscosimeter at 20 rpm/min, and the composition can be used to an ink for screen printing.

The invention further relates to a conductive liquid composition wherein the viscosity of the conductive liquid composition is from 1.0 to 60 Pa·s when measured at 25±1° C. by a BH-type rotating viscosimeter at 20 rpm/min, and the composition can be used to an ink for pad printing.

The invention still further relates to a conductive liquid composition wherein the organometallic compound is a dibutyltin compound.

The invention still further relates to a conductive liquid composition wherein the coupling agent is a silane coupling agent.

The invention still further relates to a conductive liquid composition wherein the polyisocyanate is a block polyisocyanate having a curing reaction starting temperature of not less than 90° C.

The invention still further relates to a conductive liquid composition wherein the conductive liquid composition contains dimethylsilicon oil at from over 0 to 0.02 massa.

The invention still further relates to an article having a coating layer of the conductive liquid composition.

The invention still further relates to a method for producing an article wherein an article is produced by coating the conductive liquid composition.

DETAILED DESCRIPTION FOR CARRYING OUT THE INVENTION

The conductive resin composition of the invention contains (A), for a binder resin, from 5 to 25 mass % of a hydroxyl-containing resin with a hydroxyl value from 3 to 100 and a weight-average molecular weight from 4000 to 20000.

The resin is one that, by addition of the curing agents, curing accelerators and coupling agents mentioned below, has excellent firm adhesion to a wide range of substrates including PET (polyester) resin substrates, PC (polycarbonate) resin substrates, polyimide resin substrates and polyolefin resin substrates, and flexibility that can adequately withstand bending and folding, and it is an essential component of the binder resin in the conductive liquid composition of the invention.

Here, if the hydroxyl value is less than 3, crosslinking reaction will not take place sufficiently even if the curing agent, curing accelerator and coupling agent described below are added, and the adhesiveness on substrates and resistance to rinsing with MEK and the like will also be impaired, on the other hand, when it is more than 100, the crosslinking reaction will take place too rapidly, greatly shortening the pot life or extremely impairing the humidity resistance or alkali resistance.

Examples of such resins include polyester resins, acrylic resins, epoxy resins, urethane resins and amic acid resins, any of which resins may be used alone or in combinations of two or more.

Polyester resins are most preferred among such hydroxyl-containing resins.

The weight-average molecular weight of the resin is from 4000 to 20000, preferably from 6000 to 18000 and more preferably from 7000 to 16000.

When the weight-average molecular weight is less than 4000, the adhesion onto different substrates will be inferior even if it is used in combination with a curing agent, curing accelerator and coupling agent, and the resistance to rinsing with MEK (methyl ethyl ketone) or the like will also be inferior.

On the other hand, when the weight-average molecular weight is more than 20000, the viscosity of the conductive liquid composition will be increased, impairing the surface smoothness or resulting in poor coating work efficiency.

The resin content may be from 5 to 25 mass %, preferably from 8 to 20 mass % and more preferably from 10 to 15 mass % with respect to the total amount of conductive resin composition.

When the resin content is less than 5 mass %, the adhesion on different substrates may be impaired, or the resistance to rinsing with MEK or the like may be impaired, or deterioration in the surface smoothness due to irregularities in the conducting material as described below may become apparent. On the other hand, when the resin content is more than 25 mass %, the viscosity of the conductive liquid composition will be increased, impairing the surface smoothness or resulting in poor coating work efficiency.

The conductive liquid composition of the invention contains (B), for a solvent, one or more solvents with boiling points of not less than 170° C. selected from among isophorone, dibasic acid esters, 3-methoxy-3-methylbutanol, 3-methoxy-3-methylbutyl acetate, ethyleneglycol monobutyl ether acetate, coal tar naphtha with a boiling point of more than 170° C., diethyleneglycolmonoethyl ether, diethyleneglycol monoethyl ether acetate, diethyleneglycol monobutyl ether, diethyleneglycol monobutyl ether acetate, triethyleneglycol monobutyl ether, triethyleneglycol monobutyl ether acetate, polyethyleneglycol dimethyl ether, tetraethyleneglycol dimethyl ether and polyethyleneglycol monomethyl ether, at not less than 70 mass % of the total solvent, but the content is preferably not less than 80 mass % and more preferably not less than 90 mass %.

Particularly preferred among these are isophorone, coal tar naphtha with a boiling point of more than 170° C., butylcellosolve acetate and dibasic acid esters (e.g. dialkyl adipate ester-containing solvents), because of their good solubility for the aforementioned polyester resins and satisfactory spreadability onto various plastic substrate and glass substrate surfaces.

Dibasic acid esters are marketed, for example, under the trade name of FlexisolvDBE by Invista.

When the solvent with a boiling point of not less than 170° C. is present at less than at least 70 mass % of the total solvent, the leveling property may be impaired and it may not be possible to obtain a high level of surface smoothness for the conductive liquid composition. In addition, with mass-producing coating by screen printing, drying of the conductive liquid composition on the screen plate will be more rapid and clogging of the screen plate will tend to occur.

Here, there are no particular restrictions on the solvents other than the solvent with a boiling point of not less than 170° C. contained in the conductive liquid composition of the invention, but in order to reduce the azeotropic evaporation rate of the solvent with a boiling point of not less than 170° C. and maintain a high level of surface smoothness, and to ensure mass production stability in screen printing coating, it is preferred to use a solvent with a boiling point of not less than 100° C., examples of such solvents including xylene, cyclohexanone, coal tar naphtha with a boiling point from 160° C. to 170° C., mineral spirits with a boiling point from 150° C. to 170° C., 1-methoxy-2-propanol, 1-methoxypropyl-2-acetate and diacetone alcohol.

The solvent of the invention only needs to contain not less than 70 mass % of a solvent with a boiling point of not less than 170° C. of the total solvent, but in order to further stabilize the printing property when a conductive pattern including a fine pattern is to be obtained by screen printing, it is desirable for the boiling point of the solvent to be not less than 190° C.

However, since using polyethyleneglycol dimethyl ether or a mineral oil or vegetable oil with a boiling point of more than 250° C. as the solvent results in a poor drying property of the coated film, thus when a solvent having a boiling point of more than 250° C. is used, it is preferably used at not more than 25 mass % of the total solvent amount.

The total amount of solvent with respect to the total amount of the conductive liquid composition of the invention (mass %) is naturally the amount other than the other components, and it is preferably at least 10 mass % in order to satisfactorily ensure surface smoothness for the coated film.

The present invention contains (C), for a curing agent, a polyisocyanate at from 1.5 to 10.0 mass %, for crosslinking reaction with the binder resin to ensure firm adhesion with the substrate, and to improve the durability against rinsing with solvents such as MEK.

Examples of polyisocyanates include polyisocyanates such as tolylene diisocyanate, xylene diisocyanate, isophorone diisocyanate and hexamethylene diisocyanate, and polyisocyanates of isophorone diisocyanate and hexamethylene diisocyanate are preferred in consideration of weather resistance, heat resistance and durability.

When the polyisocyanate content is less than 1.5 mass %, it will be impossible to obtain a sufficiently crosslinked coating film and the adhesion or MEK rinsability will be inferior, while when it is more than 10.0 mass %, unreacted curing agent will remain and similarly the adhesion or MEK rinsability will be inferior.

According to the invention, the polyisocyanate is preferably a block polyisocyanate having a curing reaction starting temperature of not less than 90° C.

If such a block polyisocyanate is added to the conductive liquid composition, crosslinking reaction will not take place up to, for example, the environmental temperature in which heating is carried out for curing and drying, thus allowing the pot life or shelf life of the conductive liquid composition in an ordinary temperature environment to be significantly lengthened.

In the case of a non-block type polyisocyanate, the pot life will usually be from about from several hours to ten or more hours.

Furthermore, in order to accomplish sufficient crosslinking reaction of the conductive liquid composition at an example of about 150° C. for 30 minutes, the invention also contains, for a curing accelerator, (D) from 0.005 to 0.1 mass % of an organometallic compound, although the content is preferably from 0.01 to 0.05 mass % and more preferably from 0.01 to 0.03 mass %.

Representative examples of organometallic compounds for the curing accelerator include organic cobalt compounds, organic molybdenum compounds, organic tin compounds and organic titanium compounds, and organic tin compounds are satisfactory, dibutyltin compounds are especially satisfactory, and dibutyltin laurate is particularly suitable, and for compounds having excellent shelf life of the conductive liquid composition and significant curing acceleration with addition in very trace amounts.

When the curing accelerator is present at less than 0.005 mass %, a reaction acceleration effect will not be obtained and adhesion defects may occur when the conductive liquid composition has been coated on a glass substrate and cured by heat drying at 150° C. for 30 minutes, while the resistance to rinsing with MEK will also be impaired. On the other hand, when the curing accelerator is present at more than 0.1 mass %, curing of the conductive liquid composition will proceed too fast at ordinary temperature, and the pot life will be very short, at about from 1 to 2 hours.

The invention also contains, for an adhesion reinforcing agent particularly for glass substrates, (E) a coupling agent at from 0.2 to 2.5 mass %, although the content is preferably from 0.3 to 2.0 mass % and more preferably from 0.4 to 2.0 mass %.

Examples of coupling agents may be given silane-based coupling agents, titanium-based coupling agents and phosphorus-based coupling agents, and silane-based coupling agents are most satisfactory according to the experience of the present inventors. The reason for this is not completely understood but is conjectured to be that the presence of Si atoms in both the silane-based coupling agent and glass substrate may contribute to their affinity.

When the coupling agent content is less than 0.2 mass %, since the absolute amount will be reduced, the adhesion on glass substrates decreases. On the other hand, when it is more than 2.5 mass %, the excess coupling agent will presumably lead to inferior adhesion onto glass and reduced resistance to rinsing with MEK.

For the purpose of having a satisfactory electromagnetic wave shield function and antistatic function and avoiding problems by electrification errors, the conductive liquid composition of the invention has a surface resistivity from 1 to 1000 Ω/sq., and more preferably from 10 to 100 Ω/sq., when the thickness of the cured film of the conductive liquid composition is 8 μm.

(G) surface resistivity (also known as "sheet resistance") of the invention is measured by forming a dry cured film of the conductive liquid composition to a thickness of 8 μm and a size of 50 mm×80 mm, on a glass substrate or a flexible polyimide substrate, flexible PET substrate or the like, and conducting measurement by the 4-terminal method based on JIS K 7194. For example, it may be measured with a "K-705RS Four-point probe meter", in which the measurement adopts the direct current four-point probe method with units of Ω/sq.

When the surface electric resistivity is less than 1 Ω/sq., the provability of interference by electrification errors, and such a state is not satisfactory, although the electromagnetic wave is shielded properly. On the other hand, when the surface electric resistivity is more than 1000 Ω/sq., the function of shielding the electromagnetic wave decreases, although the function of defending electrification is not obstructed.

The surface resistivity range of the invention is limited to from 1 to 1000 Ω/sq. when the coating layer of the conductive liquid composition has been formed to a thickness of 8 μm, but even in the case of a product with the conductive liquid composition coated to another thickness, for example, such as 10 μm or 13 μm, the used conductive liquid composition belongs to the scope of the invention as long as the surface resistivity is from 1 to 1000 Ω/sq. when the conductive liquid composition used has been formed to a coated film of 8 μm, and the other conditions of the invention are simultaneously satisfied.

In order to obtain a coating satisfying a surface resistivity from 1 to 1000 Ω/sq. and having high surface smoothness, as well as the ability to withstand rinsing with MEK and the like, the conductive liquid composition of the invention further contains (F), for conducting materials: (f1) from 2.0 to 10.0 mass % of graphite, (f2) from 5.0 to 15.0 mass % of conductive carbon black and (f3) from 20.0 to 50.0 mass % of silica particles having a mean particle size from 1.0 to 7.0 μm and surface-coated with silver, the more preferred ranges being (f1) from 3.0 to 7.0 mass % of graphite, (f2) from 7.0 to 12.0 mass % of conductive carbon black and (f3) from 30.0 to 45.0 mass % of silica particles having a mean particle size from 1.5 to 6.0 μm and surface-coated with silver.

(f1) graphite used preferably has a mean particle size of not more than about 8 μm, since the conductive resin composition of the invention may be used even in the case of a thin-film of about 8 μm.

When the graphite content is not more than 2.0 mass %, it will be difficult to obtain a satisfactory balance of conductive function in the conductive liquid composition, on the other hand, when it is more than 10.0 mass %, the amount of sedimentation will undesirably increase.

(f2) In conductive carbon black including ketjen black, a primary particle size is generally from 10 to 100 nm and a secondary particle structure is a structure with primary particles connected in chains, a longer structure with associated has more excellent conductive function. According to the invention, the average length of the structure is preferably about from 20 to 60 μm in order to ensure a balance between conductive function, dispersibility and surface smoothness.

When the content of the conductive carbon black is less than 5.0 mass %, the conductive liquid composition coating layer will be less likely to have a high degree of surface smoothness, presumably for the reasons described in paragraph [0045] below, on the other hand, when it is more than 15.0 mass %, the dispersion time will be undesirably lengthened.

Since (f3) silver-coated silica particles have nearly spherical shapes, the mean particle sizes must be less than 8 μm, or from 1.0 to 7.0 μm, and are more preferably from 1.5 to 6.0 μm.

When the content of the silver-coated silica is more than 50 mass %, the abrasion resistance and MEK rinsing resistance of the conductive liquid composition coating layer will be inferior, and the viscosity of the conductive liquid composition will also be too high, thus hampering the coating operation. On the other hand, when the content is less than 20.0 mass %, of course, obtaining sufficient conductive function becomes difficult and such a state is undesirable.

All of the aforementioned conducting materials used may be purchased commercial products.

(f1) graphite as the conducting material has a suitable conductive function, but because of its high specific gravity, when used alone, problem of easily precipitating in the conductive liquid composition may not be avoided.

Moreover, mere addition of (f1) graphite and (f2) conductive carbon black cannot stably satisfy the condition of a surface resistivity from 1 to 1000 Ω/sq. regulated by the invention.

While (f2) conductive carbon black does not have a high conductive function, the present inventors have found that it has a property of exhibiting high surface smoothness in the conductive liquid composition of the invention. The reason of the smoothness is not certain, and it may be presumed that by addition of the specific conductive carbon black as is described above the configurations of the other included filler particles and the resin molecules are controlled during film formation with the conductive liquid composition, resulting to surprisingly satisfactory surface smoothness.

(f3) silver-coated silica particles used for the invention are preferably ones formed by electroless plating and having a mean particle size from 1.0 to 7.0 μm. The silver-coated silica is highly superior for adjustment of electric resistivity, but when its content is high, the abrasion resistance and MEK rinsing resistance will be inferior and the viscosity of the conductive liquid composition will also be too high, thus hampering the coating operation. Naturally, when the content is reduced, on the other hand, it will not be possible to obtain an adequate conductive function.

Also, when the mean particle size of the (f3) silver-coated silica particles is less than 1.0 μm, the dispersibility will tend to be impaired and the conductive function will be slightly reduced. On the other hand, when it is more than 7.0 μm, coating the conductive liquid composition to a film thickness of 8 μm may adversely affect the surface smoothness.

As a result of repeated experiments with consideration of the aspects mentioned above, the present inventors have discovered that in order to obtain a conductive coated film satisfying the conductive function specified by the invention (a surface resistivity from 1 to 1000 Ω/sq.), and having a high level of surface smoothness even as a thin-film of 8 μm while also being able to withstand rinsing with MEK and the like, it is necessary for the conductive liquid composition to contain, as conducting materials, (f1) from 2.0 to 10.0 mass % of graphite, (f2) from 5.0 to 15.0 mass % of conductive carbon black and (f3) from 20.0 to 50.0 mass % of silica particles surface-coated with silver, with a mean particle size from 1.0 to 7.0 μm, and the invention has been completed upon said discovery.

Especially it should be remarkable to have discovered that by including as an essential component of (f2) conductive carbon black, which does not have a high conductive function, a surprisingly high level of surface smoothness is obtained even with a low film thickness, as is described in paragraph above.

Moreover, by adjustment to a conductive liquid composition with a viscosity from 0.1 to 100 Pa·s when measured at 25±1° C. by a BH-type rotating viscosimeter at 20 rpm/min, the invention can be suitably used as to ink for screen printing.

When the viscosity is less than 0.1 Pa·s, the ink will tend to flow off from the image pattern on the screen plate, resulting in extremely poor image precision, on the other hand, when it is more than 100 Pa·s, the surface smoothness will be impaired and satisfactory printing will not be possible unless the printing speed is extremely reduced.

Furthermore, by adjustment to a conductive liquid composition with a viscosity from 1.0 to 60 Pa·s when measured at 25±1° C. by a BH-type rotating viscosimeter at 20 rpm/min, the invention can be suitably used to an ink for pad printing.

When the viscosity is less than 1.0 Pa·s, the ink transfer volume onto the pad will be reduced and it will be difficult to accomplish satisfactory pad printing, on the other hand, when it is more than 60 Pa·s, stringing of the ink between the plate and the pad will be more likely to occur and it will be difficult to obtain the desired printed image.

The method for coating the conductive liquid composition of the invention is not limited to screen printing and pad printing methods, and coating may instead be carried out by, for example, spray coating, dispenser coating, gravure printing or flexographic printing, if the viscosity has been adjusted to about from 0.1 to 1.0 Pa·s.

The present invention may also contain a dimethylsilicon oil at from over 0 to 0.02 mass %, in order to minimize formation of air bubbles during high-speed coating or high-speed printing of the conductive liquid composition.

When the amount of addition exceeds 0.02 mass %, care must be taken for the phenomenon of oil film bubbles in post-processing steps such as attachment of adhesive tape may cause the adhesive force of the adhesive tape to be reduced.

The present invention further provides articles with the conductive liquid composition of the invention coated on a flexible thermoplastic resin film or sheet substrate such as PET, PC, polypropylene, polyethylene or polyimide, or a glass substrate.

The present invention still further provides a method for producing an article wherein the article is produced by coating the conductive liquid composition of the invention on a flexible thermoplastic resin film or sheet substrate such as PET, PC, polypropylene, polyethylene or polyimide, or a glass substrate.

Examples

Examples and Comparative Examples of the invention are shown in [Table 1] below. However, the invention is not limited to these examples.

The conductive liquid compositions of the examples and comparative examples in Table 1 were produced by precisely measuring out the materials in the amounts listed in the table into a production vessel, subsequently stirring with a propeller rotating stirrer until the material became thoroughly uniform, and then forming a dispersion by 2 passes with a triple roll mill.

TABLE 1

| | Example 1 | Example 2 | Example 3 | Example 4 | Example 5 | Example 6 | Example 7 | Example 8 | Example 9 | Example 10 |
|---|---|---|---|---|---|---|---|---|---|---|
| <Resin> | | | | | | | | | | |
| Polyester resin (hydroxyl value: 15) | | 15.000 | 13.000 | 10.000 | 15.000 | | 5.000 | | 15.000 | 25.000 |
| Epoxy resin (hydroxyl value: 3) | 5.000 | | | | 5.000 | | | 15.000 | | |
| Amic acid resin (hydroxyl value: 100) | | 10.000 | | | | 15.000 | | | | |
| Acryl resin (hydroxyl value: 120) | | | | | | | | | | |
| Solvent | | | | | | | | | | |
| DBE (boiling point: 203-245° C.) | | | 10.000 | 21.960 | 20.000 | | 15.000 | | 10.000 | 10.000 |
| Coal tar naphtha (boiling point: 195-245° C.) | | 4.000 | 6.000 | | | | | 10.000 | | |
| Ethyleneglycol monobutyl ether acetate (boiling point: 190-195° C.) | 20.000 | 3.400 | 16.982 | | 5.000 | | | | | |
| Isophorone (boiling point: 216° C.) | 20.000 | | | | | 14.000 | | 18.982 | 10.000 | 10.000 |
| Polyethylene glycol dimethyl ether (boiling point: 264-294° C.) | 6.500 | | | | | | | 3.295 | 6.585 | 4.920 |
| Cyclohexanone (boiling point: 156° C.) | 19.795 | 3.000 | | | 5.579 | | | 1.000 | | |
| Diacetone alcohol (boiling point: 168° C.) | | | 1.000 | | | 3.460 | | | | |
| <Curing agent> | | | | | | | | | | |
| Non-blocked polyisocyanate (hexamethylene diisocyanate) | | 10.000 | | 5.000 | | | 1.500 | | | |
| 120° C. Block polyisocyanate (hexamethylene diisocyanate) | 1.500 | | 3.000 | | 4.000 | 5.000 | | 5.000 | 4.000 | 2.500 |
| <Curing accelerator> | | | | | | | | | | |
| Dibutyltin compound | 0.005 | 0.100 | 0.015 | 0.020 | 0.020 | 0.020 | 0.005 | 0.015 | 0.015 | 0.050 |
| <Coupling agent> | | | | | | | | | | |
| Silane coupling agent | 0.200 | 2.500 | 0.500 | 1.000 | 0.400 | 0.500 | 0.200 | 0.500 | 0.400 | 0.500 |
| <Conductive material> | | | | | | | | | | |
| Graphite (mean particle size: 8 μm) | 2.000 | 10.000 | 4.500 | 2.000 | 5.000 | 2.000 | 10.000 | 5.000 | 4.000 | 2.000 |
| Conductive Ketjen carbon black (mean structure length: 50 μm) | 5.000 | 15.000 | 10.000 | 5.000 | 5.000 | 10.000 | 15.000 | 10.000 | 10.000 | 5.000 |
| Surface silver-coated silica (mean particle size: 7 μm) | 20.000 | 27.000 | 35.000 | 50.000 | 20.000 | | 25.000 | 20.000 | | 10.000 |
| Surface silver-coated silica (mean particle size: 1 μm) | | | | | 20.000 | 50.000 | 25.000 | 14.500 | 40.000 | 30.000 |
| <Antifoaming agent> | | | | | | | | | | |
| Dimethylsilicone oil | | | 0.003 | 0.020 | 0.001 | 0.020 | | 0.003 | | 0.030 |
| <Total content (mass %)> | 100.000 | 100.000 | 100.000 | 100.000 | 100.000 | 100.000 | 100.000 | 100.000 | 100.000 | 100.000 |
| Viscosity [Pa·s] | 0.10 | 100.00 | 29.00 | 60.00 | 35.00 | 75.00 | 70.00 | 30.00 | 35.00 | 25.00 |
| Measured electric resistivity [Ω/sq.] | 1000.00 | 537.43 | 23.77 | 3.65 | 20.95 | 96.28 | 8.68 | 53.45 | 70.55 | 65.70 |
| Measured surface roughness [μm] | 0.79 | 0.43 | 0.58 | 0.75 | 0.70 | 0.49 | 0.56 | 0.51 | 0.48 | 0.77 |
| <Performance evaluation> | | | | | | | | | | |
| Adhesion on polyimide film substrate | G | G | G | G | G | G | G | G | G | G |
| Adhesion on glass substrate | G | G | G | G | G | G | G | G | G | G |
| Flexibility | G | G | G | G | G | G | G | G | G | G |
| Surface smoothness | G | G | G | G | G | G | G | G | G | G |
| MEK rinsing resistance | G | G | G | G | G | G | G | G | G | G |
| Conductive function | G | G | VG | G | VG | VG | G | VG | VG | VG |

| | Comp. Example 1 | Comp. Example 2 | Comp. Example 3 | Comp. Example 4 | Comp. Example 5 | Comp. Example 6 | Comp. Example 7 | Comp. Example 8 |
|---|---|---|---|---|---|---|---|---|
| <Resin> | | | | | | | | |
| Polyester resin (hydroxyl value: 15) | | 3.000 | | | 10.000 | 5.000 | 15.000 | 10.000 |
| Epoxy resin (hydroxyl value: 3) | | | 15.000 | 5.000 | | | 10.000 | 10.000 |
| Amic acid resin (hydroxyl value: 100) | | | | | | 10.000 | | |
| Acryl resin (hydroxyl value: 120) | | 15.000 | | | | | | |
| Solvent | | | | | | | | |
| DBE (boiling point: 203-245° C.) | 30.000 | 20.000 | | 21.960 | 15.000 | | 34.470 | 34.470 |
| Coal tar naphtha (boiling point: 195-245° C.) | | | | 4.000 | | 4.000 | | |
| Ethyleneglycol monobutyl ether acetate (boiling point: 190-195° C.) | | | 5.000 | | | 3.400 | | |
| Isophorone (boiling point: 216° C.) | | | | 18.982 | | 2.400 | | |
| Polyethylene glycol dimethyl ether (boiling point: 264-294° C.) | | | | | | 3.297 | | |
| Cyclohexanone (boiling point: 156° C.) | | 4.870 | 5.579 | 1.000 | | | | |
| Diacetone alcohol (boiling point: 168° C.) | | | | | 10.000 | | | |

TABLE 1-continued

| | | | | | | | | |
|---|---|---|---|---|---|---|---|---|
| <Curing agent> | | | | | | | | |
| Non-blocked polyisocyanate (hexamethylene diisocyanate) | 5.000 | | | 1.000 | 1.500 | 10.000 | | |
| 120° C. Block polyisocyanate (hexamethylene diisocyanate) | | 4.000 | 5.000 | | | | 5.000 | 5.000 |
| <Curing accelerator> | | | | | | | | |
| Dibutyltin compound | 0.100 | 0.020 | 0.015 | 0.020 | 0.003 | 0.100 | 0.030 | 0.030 |
| <Coupling agent> | | | | | | | | |
| Silane coupling agent | 2.000 | 0.400 | 0.500 | 1.000 | 0.200 | 0.100 | 0.500 | 0.500 |
| <Conductive material> | | | | | | | | |
| Graphite (mean particle size: 8 μm) | 5.000 | 5.000 | 5.000 | 2.000 | 10.000 | 10.000 | 10.000 | 5.000 |
| Conductive Ketjen carbon black (mean structure length: 50 μm) | 10.000 | 5.000 | 10.000 | 5.000 | 15.000 | 15.000 | 15.000 | 3.000 |
| Surface silver-coated silica (mean particle size: 7 μm) | 40.000 | 20.000 | 20.000 | 50.000 | 25.000 | 30.000 | 10.000 | 20.000 |
| Surface silver-coated silica (mean particle size: 1 μm) | | 20.000 | 14.500 | | 25.000 | | 5.000 | 20.000 |
| <Antifoaming agent> | | | | | | | | |
| Dimethylsilicone oil | 0.030 | 0.001 | 0.003 | 0.020 | | | | |
| <Total content (mass %)> | 100.000 | 100.000 | 100.000 | 100.000 | 100.000 | 100.000 | 100.000 | 108.000 |
| Viscosity [Pa · s] | 5.00 | 31.00 | 35.00 | 62.00 | 70.00 | 100.00 | 25.00 | 30.00 |
| Measured electric resistivity [Ω/sq.] | 25.33 | 28.48 | 55.00 | 4.50 | 8.68 | 595.00 | 1500.00 | 65.00 |
| Measured surface roughness [μm] | 0.61 | 0.71 | 1.15 | 0.78 | 0.56 | 0.48 | 0.49 | 1.53 |
| <Performance evaluation> | | | | | | | | |
| Adhesion on polyimide film substrate | G | G | G | P | G | G | G | G |
| Adhesion on glass substrate | F | G | G | P | F | P | G | G |
| Flexibility | G | G | G | G | G | G | G | G |
| Surface smoothness | G | G | F | G | G | G | G | F |
| MEK rinsing resistance | P | F | G | P | F | P | G | G |
| Conductive function | VG | VG | VG | G | G | G | F | VG |

The evaluated properties and evaluation methods are described below.

The coated film was formed by screen printing (coating area: 80 mm×50 mm rectangle, coated film thickness after drying curing: 8 μm), and dry curing was carried out at 150° C. for 30 minutes.

《Adhesion onto Polyimide Film Substrate》

The coated film on a flexible polyimide substrate with a thickness of 125 μm was subjected to a crosscut cellophane tape peeling test on a grid with 100 pieces of 1 mm-squares (hereunder referred to simply as "grid peeling test"), and to a scratch peeling test with the fingernail (hereunder referred to simply as "fingernail peeling test," with an evaluation of "G" to be satisfactory.

G: Absolutely no peeling in grid peeling test or fingernail peeling test.

F: Slight peeling occurred in grid peeling test or fingernail peeling test.

P: Obvious peeling occurred in grid peeling test or fingernail peeling test.

《Adhesion onto Glass Substrate》

The coated film on a 2 mm-thick glass substrate was subjected to a grid peeling test and a fingernail peeling test, with an evaluation of "G" being considered satisfactory.

G: Absolutely no peeling in grid peeling test or fingernail peeling test.

F: Slight peeling occurred in grid peeling test or fingernail peeling test.

P: Obvious peeling occurred in grid peeling test or fingernail peeling test.

《Flexibility》

The coated film on a flexible polyimide substrate with a thickness of 125 μm was subjected to 180° folding three times, together with a polyimide substrate, and the outer appearance of the coated film was observed while changes in the electric resistivity were measured, with an evaluation of "G" being considered satisfactory.

G: No abnormal outer appearance, change in electric resistivity of less than ±5%.

F: No abnormal outer appearance, but change in electric resistivity of not less than ±5%.

P: Abnormalities in outer appearance such as cracking.

《Surface Smoothness》

The surface roughness of the coated film on a flexible polyimide substrate with a thickness of 125 μm was measured with a surface roughness measuring instrument SV-600 by Mitsutoyo Corporation.

G: Less than 0.8 μm.

F: Less than from 0.8 to 2.0 μm.

P: Not less than 2.0 μm.

《MEK Rinsing Resistance》

The coated film on a flexible polyimide substrate with thickness of 125 μm was immersed for 1 hour in an MEK solution, and then the outer appearance of the coated film was observed while changes in the electric resistivity were measured, with an evaluation of "G" to be satisfactory.

G: No abnormal outer appearance, change in electric resistivity of less than ±5%.

F: No abnormal outer appearance, but change in electric resistivity of not less than ±5%.

P: Abnormalities in outer appearance such as dissolution, blistering, notable change in luster.

《Conductive Function (Surface Resistivity)》

The coated film on a flexible polyimide substrate with a thickness of 125 μm was subjected to potential resistivity measurement by a K-705RS four-point probe meter of Kyowa Riken Co., Ltd. using the direct-current four-point probe method, with an evaluation of VG or G to be satisfactory.

VG: From 10 to 100 Ω/sq.
G: From 1 to less than 10 Ω/sq., or over 100 to 1000 Ω/sq.
F: Less than 1 Ω/sq., or more than 1000 Ω/sq.

As shown in Table 1, with the conductive liquid compositions of the examples, it was possible to manufacture articles simultaneously satisfying the required performance aspects mentioned in paragraph above, and having satisfactory electromagnetic wave shield functions and antistatic functions.

In addition, when the conductive liquid resin composition of Example 5 was used to form a coating layer with a dry cured film thickness of 8 μm on a flexible imide film substrate by pad printing, it was possible to manufacture articles simultaneously satisfying the required performance aspects mentioned above and having a satisfactory electromagnetic wave shield functions and antistatic functions, similar to Example 5.

What is claimed is:

1. A conductive liquid composition comprising:
   (A) for a binder resin, from 5 to 25 mass % of a hydroxyl-containing resin with a hydroxyl value from 3 to 100 and a weight-average molecular weight from 4000 to 20000,
   (B) for a solvent, at least one type of solvent, each with a boiling point of not less than 170° C. selected from the group consisting of isophorone, dibasic acid esters, 3-methoxy-3-methylbutanol, 3-methoxy-3-methylbutyl acetate, ethyleneglycol monobutyl ether acetate, coal tar naphtha with a boiling point of more than 170° C., diethyleneglycol monoethyl ether, diethyleneglycol monoethyl ether acetate, diethyleneglycol monobutyl ether, diethyleneglycol monobutyl ether acetate, triethyleneglycol monobutyl ether, triethyleneglycol monobutyl ether acetate, polyethyleneglycol dimethyl ether, tetraethyleneglycol dimethyl ether and polyethyleneglycol monomethyl ether, at not less than 70 mass % of the total solvent,
   (C) for a curing agent, from 1.5 to 10.0 mass % of polyisocyanate,
   (D) for a curing accelerator, from 0.005 to 0.1 mass % of an organometallic compound,
   (E) for an adhesion reinforcing agent, from 0.2 to 2.5 mass % of a coupling agent,
   (F) for conducting materials:
      (f1) from 2.0 to 10.0 mass % of graphite,
      (f2) from 5.0 to 15.0 mass % of conductive carbon black, and
      (f3) from 20.0 to 50.0 mass % of silica particles with a mean particle size from 1.0 to 7.0 μm and surface-coated with silver, and
   (G) a surface resistivity from 1 to 1000 Ω/sq when the thickness of the cured film of the conductive liquid composition is 8 μm.

2. The conductive liquid composition according to claim 1, wherein the conductive liquid composition has a viscosity from 0.1 to 100 Pa·s when measured at 25±1° C. by a BH-type rotating viscosimeter at 20 rpm/min, and the composition is adapted to be used for an ink for screen printing.

3. The conductive liquid composition according to claim 1, wherein the conductive liquid composition has a viscosity from 1.0 to 60 Pa·s when measured at 25±1° C. by a BH-type rotating viscosimeter at 20 rpm/min, and the composition is adapted to be used to for an ink for pad printing.

4. The conductive liquid composition according to claim 1, wherein the organometallic compound is a dibutyltin compound.

5. The conductive liquid composition according to claim 1, wherein the coupling agent is a silane coupling agent.

6. The conductive liquid composition according to claim 1, wherein the polyisocyanate is a block polyisocyanate having a curing reaction starting temperature of not less than 90° C.

7. The conductive liquid composition according to claim 1, wherein the conductive liquid composition further contains dimethylsilicon oil at from over 0 to 0.02 mass %.

8. An article having a coating layer of the conductive liquid composition according to claim 1.

9. A method for producing an article comprising the step of producing the article by depositing the conductive liquid composition according to claim 1 onto a material for coating.

* * * * *